US012810982B2

(12) United States Patent
Finley et al.

(10) Patent No.: US 12,810,982 B2
(45) **Date of Patent: *Nov. 24, 2026**

(54) HOME CONDITION ALERTS BASED ON HOME SENSOR DATA

(71) Applicant: STATE FARM MUTUAL AUTOMOBILE INSURANCE COMPANY, Bloomington, IL (US)

(72) Inventors: Eric Allyn Finley, Bloomington, IL (US); Jennifer L. Crawford, Normal, IL (US); Corin Rebekah Chapman, Bloomington, IL (US); Edward W. Breitweiser, Bloomington, IL (US); Gregory Wong, New Albany, OH (US)

(73) Assignee: STATE FARM MUTUAL AUTOMOBILE INSURANCE COMPANY, Bloomington, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/929,138

(22) Filed: Oct. 28, 2024

(65) Prior Publication Data

US 2025/0054594 A1 Feb. 13, 2025

Related U.S. Application Data

(63) Continuation of application No. 18/099,620, filed on Jan. 20, 2023, now Pat. No. 12,154,670.

(Continued)

(51) Int. Cl.

*G16H 20/00* (2018.01)
*B60S 5/00* (2006.01)

(Continued)

(52) U.S. Cl.

CPC ................ *G16H 20/00* (2018.01); *B60S 5/00* (2013.01); *G06T 7/20* (2013.01); *G06T 11/00* (2013.01);

(Continued)

(58) Field of Classification Search

CPC ........... G06N 20/00; G06N 3/00; G06N 5/00; G06N 7/00; G06N 10/00; G06N 99/00;

(Continued)

(56) References Cited

U.S. PATENT DOCUMENTS 9,830,748 B2 11/2017 Rosenbaum
9,990,782 B2 6/2018 Rosenbaum (Continued)

FOREIGN PATENT DOCUMENTS

EP 3239686 A1 11/2017
EP 3578433 B1 8/2020

(Continued)

*Primary Examiner* — Daniel Previl

(74) *Attorney, Agent, or Firm* — MARSHALL, GERSTEIN & BORUN LLP

(57) ABSTRACT

Techniques for generating alerts related to unsafe/unhealthy home conditions may include monitoring sensor data associated with a home environment over a period of time; analyzing the sensor data associated over the period in order to identify an unsafe/unhealthy condition associated with the home environment over the period; obtaining sensor data associated with a resident of the home environment over the period; determining that the resident of the home environment is not physically present at the home environment over the period; upon identifying an unsafe/unhealthy condition associated with the home environment over the period and determining that the resident of the home environment is not physically present at the home environment over the period, generating an alert indicating the identified unsafe or unhealthy condition associated with the home environment over the period; and transmitting the alert to a computing device associated with the resident of the home environment.

11 Claims, 3 Drawing Sheets

Related U.S. Application Data

(60) Provisional application No. 63/428,723, filed on Nov. 29, 2022, provisional application No. 63/427,596, filed on Nov. 23, 2022, provisional application No. 63/427,495, filed on Nov. 23, 2022, provisional application No. 63/427,680, filed on Nov. 23, 2022.

(51) Int. Cl.

| | |
|---|---|
| ***G06T 7/20*** | (2017.01) |
| ***G06T 11/00*** | (2006.01) |
| ***G06V 20/20*** | (2022.01) |
| ***G07C 5/08*** | (2006.01) |
| ***G08B 21/04*** | (2006.01) |
| ***G08B 21/18*** | (2006.01) |
| ***G08B 21/22*** | (2006.01) |
| ***G08B 31/00*** | (2006.01) |
| ***G16H 40/67*** | (2018.01) |
| ***G16H 50/20*** | (2018.01) |

(52) U.S. Cl.

CPC ........... *G06V 20/20* (2022.01); *G07C 5/0808* (2013.01); *G08B 21/0476* (2013.01); *G08B 21/0484* (2013.01); *G08B 21/182* (2013.01); *G08B 21/22* (2013.01); *G08B 31/00* (2013.01); *G16H 40/67* (2018.01); *G16H 50/20* (2018.01); *G06T 2200/24* (2013.01); *G06T 2207/30268* (2013.01)

(58) Field of Classification Search

CPC .......... G06N 3/08; G06N 20/10; G06N 3/045; G06N 3/084; G06N 3/126; G06N 5/01; G06N 7/01; G06N 5/04; G08B 13/19613; G08B 17/10; G08B 21/0423; G08B 25/08; G08B 21/0476; G08B 21/0484; G08B 21/182; G08B 21/22; G08B 29/186; G08B 31/00; G08B 1/00; G08B 3/00; G08B 5/00; G08B 6/00; G08B 7/00; G08B 9/00; G08B 13/00; G08B 15/00; G08B 17/00; G08B 19/00; G08B 21/00; G08B 23/00; G08B 25/00; G08B 26/00; G08B 27/00; G08B 29/00; G08B 13/19602; G08B 25/008; G08B 25/14; G08B 21/0205; G08B 25/005; B60S 5/00; B60S 1/00; B60S 3/00; B60S 9/00; B60S 13/00; B60S 11/00; G06T 11/00; G06T 2200/24; G06T 2207/30268; G06T 7/20; G06T 1/00; G06T 3/00; G06T 5/00; G06T 7/00; G06T 9/00; G06T 12/00; G06T 13/00; G06T 15/00; G06T 17/00; G06T 19/00; G06T 2200/00; G06T 2201/00; G06T 2207/00; G06T 2210/00; G06T 2211/00; G06T 2213/00; G06T 2215/00; G06T 2219/00; G06V 20/20; G06V 10/00; G06V 20/00; G06V 30/00; G06V 40/00; G06V 2201/00; G06V 40/20; G06V 20/52; G06V 20/10; G06V 20/68; G07C 5/0808; G07C 1/00; G07C 3/00; G07C 5/00; G07C 7/00; G07C 9/00; G07C 11/00; G07C 13/00; G07C 15/00; G07C 2205/00; G07C 2209/00; G16H 20/00; G16H 40/67; G16H 50/20; G16H 10/00; G16H 15/00; G16H 30/00; G16H 40/00; G16H 50/00; G16H 70/00; G16H 80/00; G16H 10/60; G16H 50/30; G16H 50/50; G16H 50/70; G16H 50/80; G16H 40/20; G06F 16/9538; G06F 16/9577; G06F 1/00; G06F 3/00; G06F 5/00; G06F 7/00; G06F 8/00; G06F 9/00; G06F 15/00; G06F 16/00; G06F 17/00; G06F 18/00; G06F 21/00; G06F 2111/00; G06F 2113/00; G06F 2115/00; G06F 2117/00; G06F 2119/00; G06F 2123/00; G06F 16/283; G06F 2221/2111; G06F 30/13; G06F 30/27; G06F 16/24578; G06F 16/3329; G06F 21/31; G06F 21/74; G06F 21/88; G06F 2221/2137; G06F 40/284; G06F 40/30; G06F 40/35; G06F 8/38; G06F 9/451; G06Q 30/0201; G06Q 30/0251; G06Q 30/0282; G06Q 10/00; G06Q 20/00; G06Q 30/00; G06Q 40/00; G06Q 50/00; G06Q 90/00; G06Q 99/00; G06Q 2220/00; G06Q 2230/00; G06Q 2240/00; G06Q 2250/00; G06Q 10/06; G06Q 10/0639; G06Q 10/101; G05B 15/02; G05B 2219/2642; G05B 17/02; H04L 12/2803; H04L 12/2827; H04L 2209/805; H04L 43/0811; H04L 43/0894; H04L 43/10; H04L 9/0872; H04L 9/0894; H04L 9/3226; H04N 21/43615; H04N 21/44213; H04N 21/478; H04N 23/633; H04N 5/445; H04N 7/183; H05B 47/155; H05B 47/195; A41D 1/002; A61B 2503/10; A61B 2503/20; A61B 2505/09; A61B 2560/0242; A61B 2562/0219; A61B 2562/04; A61B 2562/222; A61B 5/0013; A61B 5/0022; A61B 5/0059; A61B 5/0064; A61B 5/0071; A61B 5/0075; A61B 5/08; A61B 5/082; A61B 5/1112; A61B 5/112; A61B 5/1121; A61B 5/1123; A61B 5/411; A61B 5/442; A61B 5/445; A61B 5/6804; A61B 5/7267; A61B 5/7465; A61H 1/02; A61H 1/0237; A61H 1/0244; A61H 1/0274; A61H 2201/0192; A61H 2201/123; A61H 2201/1626; A61H 2201/163; A61H 2201/1638; A61H 2201/1642; A61H 2201/165; A61H 2201/50; A61H 2201/5007; A61H 2201/501; A61H 2201/5058; A61H 2201/5097; A61H 2203/0406; A61H 3/00; A63B 2024/0096; A63B 2220/12; A63B 2220/51; A63B 2220/54; A63B 2220/803; A63B 2230/04; A63B 2230/60; A63B 24/0062; B25J 9/0006; B25J 9/163; G01P 1/02; G01P 13/00; G09B 19/003; G09B 19/0038; G09B 23/28

USPC .... 340/573.4, 457, 573.1, 526, 506, 870.16, 340/539.27, 539.3, 539.31, 571, 588

See application file for complete search history.

(56) References Cited

U.S. PATENT DOCUMENTS

| | | | | |
|---|---|---|---|---|
| 10,269,190 | B2 | 4/2019 | Rosenbaum | |
| 10,467,824 | B2 | 11/2019 | Rosenbaum | |
| 11,077,436 | B1 | 8/2021 | dePillis | |
| 11,227,452 | B2 | 1/2022 | Rosenbaum | |
| 11,407,410 | B2 | 8/2022 | Rosenbaum | |
| 11,524,707 | B2 | 12/2022 | Rosenbaum | |
| 11,532,051 | B1 * | 12/2022 | Braun | G06Q 40/08 |
| 11,551,579 | B2 * | 1/2023 | Dettinger | G16H 70/20 |
| 11,594,083 | B1 | 2/2023 | Rosenbaum | |
| 11,725,971 | B2 | 8/2023 | Correnti et al. | |
| 11,769,598 | B2 | 9/2023 | Barrett et al. | |
| 12,154,670 | B2 * | 11/2024 | Finley | G06T 7/20 |

(56) References Cited

U.S. PATENT DOCUMENTS

| | | | | |
|---|---|---|---|---|
| 12,205,449 | B2 * | 1/2025 | Webb | G08B 21/0453 |
| 12,211,597 | B2 * | 1/2025 | Cowan | G06F 16/9535 |
| 2003/0222775 | A1 | 12/2003 | Rackham et al. | |
| 2006/0055543 | A1 | 3/2006 | Ganesh et al. | |
| 2007/0156626 | A1 * | 7/2007 | Roehm | G16H 80/00<br>706/924 |
| 2009/0256710 | A1 | 10/2009 | Duckert et al. | |
| 2013/0132109 | A1 | 5/2013 | Mruthyunjaya et al. | |
| 2013/0151274 | A1 * | 6/2013 | Bage | G16H 20/13<br>705/2 |
| 2016/0189531 | A1 | 6/2016 | Modi et al. | |
| 2017/0156608 | A1 | 6/2017 | Mahar | |
| 2017/0172493 | A1 | 6/2017 | Rahman et al. | |
| 2017/0351820 | A1 | 12/2017 | Van Halteren et al. | |
| 2018/0317037 | A1 | 11/2018 | Brännmark et al. | |
| 2019/0122522 | A1 | 4/2019 | Stefanski et al. | |
| 2019/0188337 | A1 | 6/2019 | Keane | |
| 2019/0249746 | A1 | 8/2019 | Saley | |
| 2019/0251805 | A1 | 8/2019 | Sankey | |
| 2019/0278992 | A1 | 9/2019 | Hossain et al. | |
| 2020/0044876 | A1 | 2/2020 | Piccolo, III et al. | |
| 2020/0357204 | A1 | 11/2020 | Crequer et al. | |
| 2021/0279475 | A1 * | 9/2021 | Tusch | G06T 7/73 |
| 2022/0092557 | A1 | 3/2022 | Antony et al. | |
| 2022/0092893 | A1 | 3/2022 | Rosenbaum | |
| 2022/0230746 | A1 | 7/2022 | Anthapur | |
| 2022/0340148 | A1 | 10/2022 | Rosenbaum | |
| 2022/0398717 | A1 * | 12/2022 | Hébert | G06N 3/09 |
| 2023/0056899 | A1 * | 2/2023 | Blanchard | G16H 10/60 |
| 2023/0060300 | A1 | 3/2023 | Rosenbaum | |
| 2023/0107712 | A1 | 4/2023 | Gil et al. | |
| 2023/0358588 | A1 | 11/2023 | Correnti et al. | |
| 2024/0156401 | A1 | 5/2024 | Harris et al. | |

FOREIGN PATENT DOCUMENTS

| | | | |
|---|---|---|---|
| EP | 3730375 | B1 | 10/2021 |
| EP | 3960576 | A1 | 3/2022 |
| EP | 4190659 | A1 | 6/2023 |
| EP | 4190660 | A1 | 6/2023 |

* cited by examiner

HOME CONDITION ALERTS BASED ON HOME SENSOR DATA

CROSS-REFERENCE TO RELATED APPLICATIONS

The present application is a continuation of U.S. patent application Ser. No. 18/099,620 filed on Jan. 20, 2023, entitled "Home Condition Alerts Based on Home Sensor Data", which claims priority to U.S. Provisional Patent Application No. 63/427,596, entitled "Homeowner Health Alerts and Mitigation based on Home Sensor Data," and filed Nov. 23, 2022; U.S. Provisional Patent Application No. 63/428,723, entitled "Homeowner Health Alerts and Mitigation based on Home Sensor Data," and filed Nov. 29, 2022; U.S. Provisional Patent Application No. 63/427,495, entitled "Home Condition Alerts based on Home Sensor Data," and filed Nov. 23, 2022; and U.S. Provisional Patent Application No. 63/427,680, entitled "Home and Vehicle Repair Diagnostics," and filed Nov. 23, 2022; the disclosures of each of which are incorporated by reference herein.

FIELD OF THE INVENTION

The present disclosure generally relates to technologies associated with home monitoring, more particularly, to technologies for generating alerts related to unsafe or unhealthy home conditions.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Sometimes it may be difficult for residents of a home environment to identify an unsafe or unhealthy condition that is developing in the home environment. In some cases, an unsafe or unhealthy condition in a home environment may develop without residents of the home environment knowing at all, especially if the residents of the home environment are not physically present in the home environment as the unsafe or unhealthy condition develops. When residents of a home environment do not realize that an unsafe or unhealthy condition is developing in the home environment, they often cannot take mitigating steps until the unsafe or unhealthy condition has become severe, at which point mitigation steps may be extensive, expensive, or even impossible. Conventional techniques may include additional inefficiencies, encumbrances, ineffectiveness, and/or other drawbacks.

SUMMARY

The present embodiments may relate to, inter alia, technologies associated with home monitoring, as well as technologies for generating alerts related to unsafe or unhealthy home conditions.

In one aspect, a computer-implemented method for generating alerts related to unsafe or unhealthy home conditions may be provided. The method may be implemented via one or more local or remote processors, transceivers, sensors, servers, memory units, vehicles, vehicle-mounted processors and sensors, mobile devices, smart contact lenses, smart watches, wearables, virtual headsets (e.g., virtual reality headsets, smart glasses, augmented reality glasses, mixed or extended reality glasses or headsets, etc.), and/or other electronic or electric components, which may be in wired or wireless communication with one another and/or other devices. In one instance, the method may include (1) monitoring, by one or more processors, sensor data associated with a home environment over a period of time; (2) analyzing, by the one or more processors, the sensor data associated with the home environment over the period of time in order to identify an unsafe or unhealthy condition associated with the home environment over the period of time; (3) obtaining, by the one or more processors, sensor data associated with a resident of the home environment over the period of time; (4) determining, by the one or more processors, based upon the sensor data associated with the resident of the home environment over the period of time, that the resident of the home environment is not physically present at the home environment over the period of time; (5) upon identifying an unsafe or unhealthy condition associated with the home environment over the period of time and determining that the resident of the home environment is not physically present at the home environment over the period of time, generating an alert, by the one or more processors, the alert indicating the identified unsafe or unhealthy condition associated with the home environment over the period of time; and/or (6) transmitting, by the one or more processors, the alert to a computing device associated with the resident of the home environment. The method may include additional, less, or alternate actions, including those discussed elsewhere herein.

In another aspect, a computer system for generating alerts related to unsafe or unhealthy home conditions may be provided. The computer system may include one or more local or remote processors, transceivers, sensors, servers, memory units, vehicles, vehicle-mounted processors and sensors, mobile devices, wearables, smart contacts, smart watches, virtual headsets (e.g., virtual reality headsets, smart glasses, augmented reality glasses, mixed or extended reality headsets or glasses, etc.), and/or other electronic or electric components, which may be in wired or wireless communication with one another and/or other devices. In one instance, the computer system may include one or more processors and a memory storing computer-executable instructions that, when executed by the one or more processors, cause the one or more processors to: (1) monitor sensor data associated with a home environment over a period of time; (2) analyze the sensor data associated with the home environment over the period of time in order to identify an unsafe or unhealthy condition associated with the home environment over the period of time; (3) obtain sensor data associated with a resident of the home environment over the period of time; (4) determine, based upon the sensor data associated with the resident of the home environment over the period of time, that the resident of the home environment is not physically present at the home environment over the period of time; (5) upon identifying an unsafe or unhealthy condition associated with the home environment over the period of time and determining that the resident of the home environment is not physically present at the home environment over the period of time, generate an alert indicating the identified unsafe or unhealthy condition associated with the home environment over the period of time; and/or (6) transmit the alert to a computing device associated with the resident of the home environment. The system may include additional, less, or alternate functionality, including that discussed elsewhere herein.

In still another aspect, a non-transitory computer-readable storage medium storing computer-readable instructions for generating alerts related to unsafe or unhealthy home conditions may be provided. The computer-readable instructions, when executed by one or more processors, cause the one or more processors to: (1) monitor sensor data associated with a home environment over a period of time; (2) analyze the sensor data associated with the home environment over the period of time in order to identify an unsafe or unhealthy condition associated with the home environment over the period of time; (3) obtain sensor data associated with a resident of the home environment over the period of time; (4) determine, based upon the sensor data associated with the resident of the home environment over the period of time, that the resident of the home environment is not physically present at the home environment over the period of time; (5) upon identifying an unsafe or unhealthy condition associated with the home environment over the period of time and determining that the resident of the home environment is not physically present at the home environment over the period of time, generate an alert indicating the identified unsafe or unhealthy condition associated with the home environment over the period of time; and/or (6) transmit the alert to a computing device associated with the resident of the home environment. The instructions may direct additional, less, or alternative functionality, including that discussed elsewhere herein.

Advantages will become more apparent to those of ordinary skill in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof.

There are shown in the drawings arrangements which are presently discussed, it being understood, however, that the present embodiments are not limited to the precise arrangements and instrumentalities shown, wherein.

Figure 1:
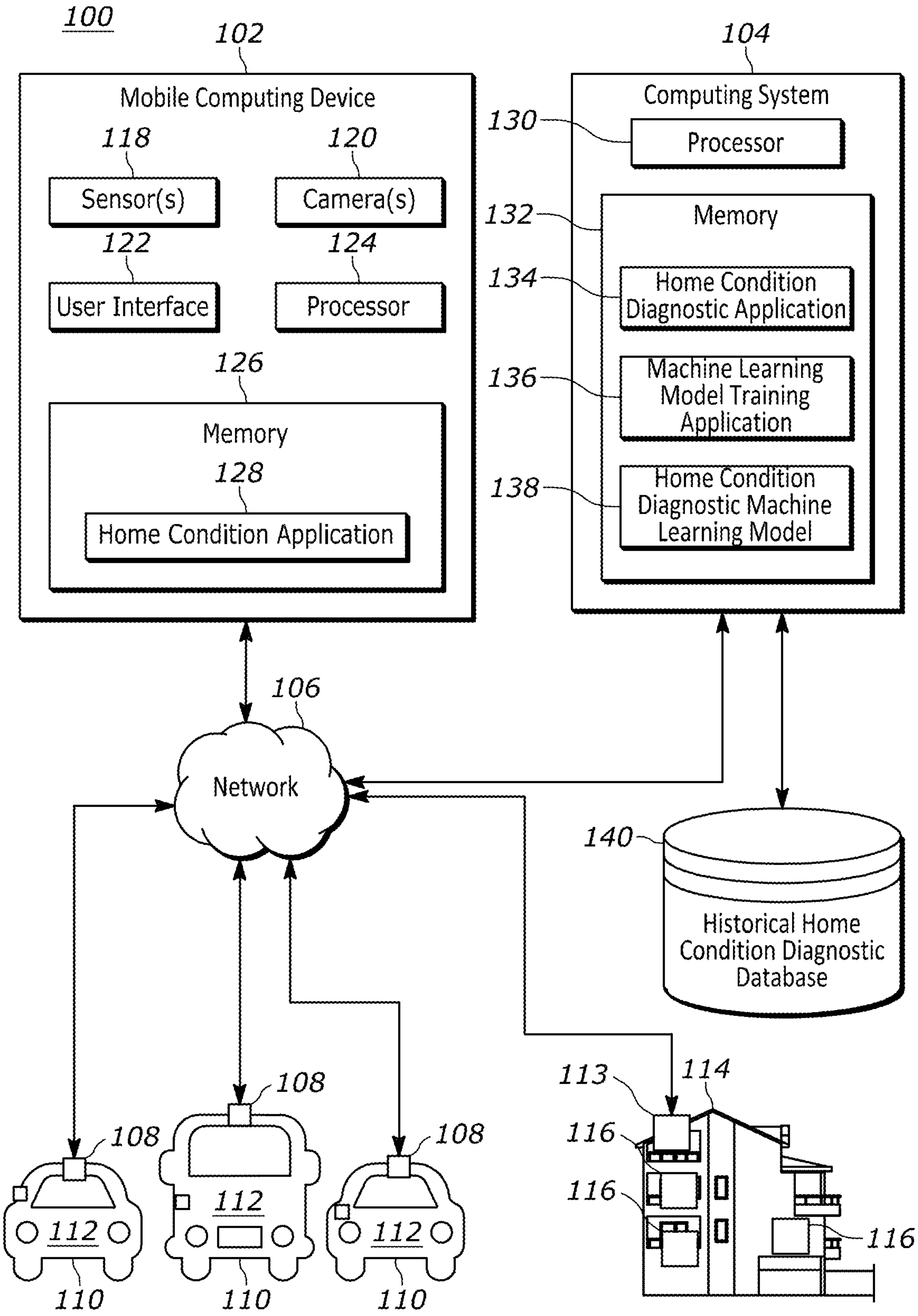
FIG. 1 depicts an exemplary computer system for generating alerts related to unsafe or unhealthy home conditions, according to one embodiment.

While the systems and methods disclosed herein is susceptible of being embodied in many different forms, it is shown in the drawings and will be described herein in detail specific exemplary embodiments thereof, with the understanding that the present disclosure is to be considered as an exemplification of the principles of the systems and methods disclosed herein and is not intended to limit the systems and methods disclosed herein to the specific embodiments illustrated. In this respect, before explaining at least one embodiment consistent with the present systems and methods disclosed herein in detail, it is to be understood that the systems and methods disclosed herein is not limited in its application to the details of construction and to the arrangements of components set forth above and below, illustrated in the drawings, or as described in the examples.

Methods and apparatuses consistent with the systems and methods disclosed herein are capable of other embodiments and of being practiced and carried out in various ways. Also, it is to be understood that the phraseology and terminology employed herein, as well as the abstract included below, are for the purposes of description and should not be regarded as limiting.

DETAILED DESCRIPTION

Using the techniques provided herein, data from internal or external home sensors, in conjunction with home operational/usage data, may be analyzed (in some cases, using a trained machine learning model) identify unsafe or unhealthy conditions developing in a home environment. The techniques provided herein may include generating and transmitting alerts to residents of the home environment based upon any detected current or future unsafe or unhealthy conditions developing in or around the home environment. In some examples, the techniques provided herein may include determining whether a resident of the home environment is physically present as the detected unsafe or unhealthy condition is developing. For instance, the alerts may be generated and/or transmitted only when a user is not in the location where the issue is developing (e.g., due to having multiple homes, or otherwise traveling/vacationing away from home, or simply being briefly outside of the home).

Additionally or alternatively, the techniques provided herein may analyze usage data or location data from a mobile device or vehicle associated with the resident of the home environment, or connectivity data between the mobile device or vehicle associated with the resident of the home environment and sensors or wireless gateways within the home environment, to determine whether the resident of the home environment is physically present at the home environment as the detected unsafe or unhealthy condition is developing.

For example, the techniques provided herein may include generating an alert to notify a user that flooding is occurring in their basement if they are not home, that their home is experiencing a power outage while they are not home (which may result in food spoilage, which the resident of the home may otherwise not notice until after eating or cooking with the spoiled food), that a lightning strike occurred near their home while they are not home, that some sort of structural damage occurred at or around the home while they are not home (which may result in unsafe or unstable areas of the home which the resident of the home may otherwise step on or lean on), etc., so that the user may be made aware of the unsafe or unhealthy condition as it develops, and in some cases initiate mitigating actions from afar or request that a friend, neighbor, or professional initiate mitigating actions.

In some cases, an alert that is generated for a resident of one home environment may be provided to residents of neighboring home environments as well. For example, when one home environment is equipped with different, or more sensitive, home monitoring sensors than others, alerts related to unsafe or unhealthy conditions that are generated based upon data from those sensors may be provided to the residents of the neighboring home environments, whose own home monitoring systems may not be capable of detecting such unsafe or unhealthy conditions.

As another example, when an unsafe or unhealthy condition develops in one home environment initially but may eventually spread to other neighboring home environments, residents of the neighboring home environments may be provided with alerts regarding the possible unsafe or unhealthy condition before their own home monitoring systems could possibly detect it, and may take steps to prevent the unsafe or unhealthy condition from occurring or mitigate its effects. For instance, an alert may initially be generated for one home in the neighborhood equipped with water sensors, indicating that the basement is flooding. An alert may then be generated for other nearby homes that may or may not be equipped with water sensors, indicating that they may be experiencing flooding (or may soon be experiencing flooding) as well. The residents of the neighboring home environments may confirm whether or not they ultimately experience the same unsafe or unhealthy conditions in their home environment, and this information may be used to further train a machine learning model to identify which conditions are likely to affect various nearby homes.

Exemplary System for Generating Alerts Related to Unsafe or Unhealthy Home Conditions Referring now to the drawings, FIG. 1 depicts an exemplary computer system 100 for generating alerts related to unsafe or unhealthy home conditions, according to one embodiment. The high-level architecture illustrated in FIG. 1 may include both hardware and software applications, as well as various data communications channels for communicating data between the various hardware and software components, as is described below.

The system 100 may include a mobile computing device 102 (which may include, e.g., a smart phone, a smart watch or fitness tracker device, a tablet, a laptop, a virtual reality headset, smart or augmented reality glasses, wearables, smart watch, mixed or extended reality glasses or headsets, etc.), a computing system 104 (which is described in greater detail below with respect to FIG. 3) one or more vehicle computing devices 108, associated with respective vehicles 110 and vehicle sensors 108, and/or one or more home computing device 113 associated with respective homes 114 and home sensors 116. The vehicles 110 may be autonomous vehicles, semi-autonomous vehicles, or connected manual vehicles, in various embodiments. In certain examples, in which the vehicles 110 are autonomous or semi-autonomous vehicles, the vehicle computing devices 108 may at least partially control the operation of the vehicles. The mobile computing device 102, computing system 104, the vehicle computing devices 108, and/or the home computing devices 113 may be configured to communicate with one another via a wired or wireless computer network 106.

Each of the vehicle computing devices 108 may include, or may be configured to communicate with, one or more respective sensors 112 associated with respective vehicles 110. For instance, the sensors 112 may include onboard interior (e.g., including the interior of the cabin of the vehicle and/or the interior of the hood and/or trunk of the vehicle) or exterior sensors. The sensors 112 may be configured to capture interior and/or exterior sensor data associated with respective vehicles 110, including image or video data (e.g., captured by one or more cameras), motion data (e.g., captured by one or more motion detectors), audio data (e.g., captured by one or more microphones), location data (e.g., captured by one or more global positioning systems [GPS] and/or other locationing systems), movement data (e.g., captured by one or more accelerometers and/or gyroscopes), temperature data (e.g., captured by one or more temperature sensors), humidity data (e.g., captured by one or more humidity sensors), air flow data (e.g., captured by one or more air flow sensors), etc.

Moreover, the sensors 112 may include sensors integrated within or positioned on various vehicle components, including but not limited to the engine, the transmission system, the battery, the alternator, the fuel system, the radiator, the axles, the suspension system, the braking system, the catalytic converter, the muffler, the tailpipe, the fuel tank, the tires, the seats, the air conditioning unit, the stereo and/or radio, the windshield wiper, the gear shift, the steering wheel, the doors, the windows and/or window controls, the sunroof, the ammeter, the clinometer, the dynamometer, the fuel gauge, the manometer, the hydrometer, the odometer (also called milometer or mileometers), the speedometer, the tachometer, the temperature gauge, the tire pressure gauge, the vacuum gauge, the voltmeter, the water temperature meter, the oil pressure gauge, the ignition system, the lighting system, the alarm, the horn, the air bag control, the fuse box, the lock system, etc.

Moreover, each of the vehicle computing devices 108 may be configured to collect (or may communicate with other devices configured to collect) vehicle operational data. For instance, the vehicle operational data may include indications of vehicle controls and/or operations performed by a vehicle operator, usage data, and/or settings adjusted by the vehicle operator for various vehicle components, as well as dates and/or times associated with controls, operations, usage, and/or settings. For instance, the operational data may include data associated with turning operations, steering operations, and/or braking operations, as well as air conditioning or heating operations, stereo or radio operations, turn signal operations, windshield wiper operators, headlight (or other lighting) operations, operations involving adjustment of vehicle seating, operations involving adjustment of vehicle mirrors, or controls, operations, usage, and/or settings adjustments of any of the vehicle components discussed above (or any other vehicle components).

Similarly, the home computing devices 113 may include, or may be configured to communicate with, one or more respective sensors 116 associated with a home environment 114. For instance, the sensors 116 may include interior sensors (e.g., including sensors positioned in various rooms of the home) or exterior sensors (e.g., including sensors positioned inside of the home and/or positioned at an exterior wall of the home and configured to capture data associated with a yard, balcony, deck, or patio of the home, and/or sensors positioned external to the home). The sensors 112 may be configured to capture interior and/or exterior sensor data associated with the home environment 114 and/or appliances or components thereof, including image or video data (e.g., captured by one or more cameras), motion data (e.g., captured by one or more motion detectors), audio data (e.g., captured by one or more microphones), movement data (e.g., captured by one or more accelerometers and/or gyroscopes), temperature data (e.g., captured by one or more temperature sensors), humidity data (e.g., captured by one or more humidity sensors), air flow data (e.g., captured by one or more air flow sensors), water flow or other water data (e.g., captured by one or more water sensors or water flow sensors), lightning or other weather conditions (e.g., captured by a lightning detector), connectivity with the mobile device 102 (e.g., captured by one or more Bluetooth beacons, WiFi gateways), etc. In some examples, the sensors may be configured to detect opening or closing of doors and/or windows in the home. Furthermore, the sensors 116 may include sensors integrated within or positioned on various home components, home appliances, plumbing fixtures, etc., including but not limited to freezers, refrigerators, water coolers, ice makers, kitchen stoves, ovens, microwave ovens, washing machines, dryers, dishwashers, air conditioners, heaters, furnaces, water heaters, ventilators, toilets, showers, sinks, sump pumps, pool heating and/or filtration equipment, etc.

Moreover, each of the home computing devices 113 may be configured to collect (or may communicate with other devices configured to collect) home operational data. For instance, the home operational data may include indications of home controls and/or operations performed by a resident of the home, usage data, and/or settings adjusted by a home resident for various home components, home appliances, plumbing fixtures, etc., as well as dates and/or times associated with such controls, operations, usage, and/or settings. For instance, the home operational data may include data associated with electricity operations or electricity usage generally, air conditioning operations or adjustment of settings associated therewith, heating operations or adjustment of settings associated therewith, water heating operations or adjustment of settings associated therewith, cooking operations or adjustment of settings associated therewith, plumbing operations or adjustment of settings associated therewith, dish washing operations or adjustment of settings associated therewith, laundry operations or adjustment of settings associated therewith, pool heating and/or filtration operations or adjustment of settings associated therewith, or any other controls, operations, usage, and/or settings adjustments of any of the home appliances, home components, and/or plumbing fixtures discussed above (or any other home appliances, home components, plumbing fixtures, etc.).

The mobile computing device 102 may include one or more sensors 118, one or more cameras 120, a user interface 122 configured to receive input from users and provide interactive displays to users, and one or more processor(s) 124, as well as one or more computer memories 126. In some examples, the one or more sensors 118 and/or the one or more cameras 120 may include any of the sensors described as vehicle sensors 112 and/or home sensors 116. Moreover, in some examples, data captured by the one or more sensors and/or the one or more cameras 120 may be used in addition to or as an alternative to any of data described as being captured by the vehicle sensors 112 and/or home sensors 116 above.

Memories 126 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others. Memorie(s) 126 may store an operating system (OS) (e.g., iOS, Microsoft Windows, Linux, UNIX, etc.) capable of facilitating the functionalities, apps, methods, or other software as discussed herein. Memorie(s) 126 may also store a home condition alert application 128.

Executing the home condition alert application 128 may include monitoring, (including receiving and/or otherwise obtaining) the sensor data captured by the vehicle sensors 112, home sensors 116, mobile device sensors 118, and/or mobile device cameras 120 over a period of time, and analyzing the sensor data, and/or vehicle operational data or home operational data over time. In particular, executing the home condition alert application 128 may include analyzing the sensor data associated with the home environment 114 (e.g., including the sensor data from the home sensors 116, mobile device sensors 118, and/or mobile device cameras 120) and/or the operational data associated with the home environment 114 over the period of time in order to identify an unsafe or unhealthy condition that exists in the home environment 114 or that may be developing in the home environment 114 over the period of time. For example, a flooding condition may be identified based upon data captured by cameras, water sensors, humidity sensors, etc. As another example, a power outage condition may be identified based upon electricity sensors or based upon operational/usage data associated with particular electric appliances in the home, or based upon a lack of sensor data from electrically powered sensors, etc. As still another example, a lightning strike may be detected based upon lightning sensors. Additionally, as another example, structural damage to the home may be captured by cameras, motion sensors, etc.

In some examples, analyzing the sensor data associated with the home environment 114 (and/or the operational data associated with the home environment 114) over the period of time in order to identify the unsafe or unhealthy condition that exists in the home environment 114 or that may be developing in the home environment 114 over the period of time may include applying a trained machine learning model to the sensor data associated with the home environment 114 (and/or the operational data associated with the home environment 114) over the period of time in order to identify the unsafe or unhealthy condition that exists in the home environment 114 or that may be developing in the home environment 114 over the period of time, e.g., by sending the sensor data (and/or operational data) to the computing system 104, on which a trained machine learning model 138 may be executing (described in greater detail below), and by receiving an identification or prediction of the unsafe or unhealthy condition that exists in the home environment 114 or that may be developing in the home environment 114 over the period of time from the computing system 104.

Furthermore, executing the home condition alert application 128 may analyzing sensor data (and/or operational data) associated with a resident of the home environment 114 over the period of time, in order to determine whether the resident of the home environment 114 is physically present at the home environment 114 over the period of time or not. The sensor data associated with the resident of the home environment 114 may include, for instance, sensor data captured by the mobile device sensors 118 and/or mobile device cameras 120 of a mobile device 102 that is specifically associated with the resident of the home environment 114, as well as vehicle operational data for a vehicle 110 specifically associated with the resident of the home environment 114, home sensor data captured by the home sensors 116, and/or home operational data, that is specifically associated with the resident of the home environment 114, and/or connectivity data related to connectivity between vehicles 110 or devices 102 specifically associated with the resident of the home environment 114 and devices that are fixed at the home environment 114 or otherwise known to be located at the home environment 114 over the period of time.

For example, if there is a single resident of the home environment 114, operational data indicating that appliances, doors, windows, etc., of the home are being used over a period of time may indicate that the resident of the home environment 114 is physically present at the home environment. As another example, if particular home appliances are specifically associated with a particular resident of the home environment 114, or require a particular resident of the home environment 114 to log in to use the home appliances, operational data indicating that these appliances are used or logged in over a period of time may indicate that the resident of the home environment 114 is physically present at the home environment 114 over the period of time. As still another example, location data captured by sensors of a mobile computing device 102 or vehicle 110 that is specifically associated with the resident of the home environment 114 may indicate a location that is not the address associated with the home environment 114 over a period of time, which may indicate that the resident of the home environment 114 is not physically present at the home environment 114 over the period of time. Similarly, operational or usage data generally from a vehicle 110 that is specifically associated with the resident of the home environment 114 over a period of time may indicate that the resident of the home environment 114 is not physically present at the home environment 114 over the period of time. Moreover, as another example, connectivity data (e.g., Bluetooth connectivity, WiFi connectivity, etc.) between devices 102 or vehicles 110 specifically associated with the resident of the home environment 114 and devices 113 or sensors 116 that are fixed at the home environment 114 or otherwise known to be located at the home environment 114 over the period of time may indicate that the resident of the home environment 114 is physically present at the home environment 114 over the period of time.

Furthermore, in some examples, analyzing the sensor data (and/or operational data) associated with the resident of the home environment 114 over the period of time in order to determine whether the resident of the home environment 114 is physically present at the home environment over the period of time may include applying a trained machine learning model to the sensor data (and/or operational data) associated with the resident of the home environment 114 over the period of time in order to determine whether the resident of the home environment 114 is physically present at the home environment over the period of time, e.g., by sending the sensor data (and/or operational data) associated with the resident of the home environment 114 to the computing system 104, on which a trained machine learning model may be executing (e.g., the trained machine learning model 138, or another machine learning model trained in a similar manner as described with respect to the trained machine learning model 138 in greater detail below), and by receiving a determination or prediction of whether the resident of the home environment 114 is physically present at the home environment over the period of time from the computing system 104.

Moreover, executing the home condition alert application 128 may include generating an alert related to the identified unsafe or unhealthy condition that exists in the home environment 114 or that may be developing in the home environment 114 over the period of time. For instance, the alert may be an audible and/or visible alert, and may include an indication of the specific identified unsafe or unhealthy condition that exists in the home environment or that may be developing in the home environment over the period of time.

The alert may be transmitted to or otherwise displayed by a user interface 122 of a mobile computing device 102 associated with the resident of the home environment 114, and in some cases may be transmitted to or otherwise displayed by other user interfaces 122 of other mobile devices 102 associated with emergency contacts, family members, or neighbors of the resident of the home environment. Moreover, in some examples, the alert may be transmitted to or otherwise displayed by other user interfaces 122 of other mobile computing devices 102 associated with nearby home environments, e.g., home environments within a specific geographic radius of the home environment 114 where the unsafe or unhealthy condition is detected.

In some examples, only specific types of unsafe or unhealthy conditions may be transmitted to or otherwise displayed by other mobile computing devices 102 associated with nearby home environments. For instance, an instance of structural damage to a particular home environment may be unlikely to spread to other nearby home environments, but an instance of flooding associated with a particular home environment may be likely to spread to other nearby home environments.

Moreover, in some examples, the geographic radius for determining other home environments to which alerts may be distributed may be modified or adjusted based upon (or may otherwise be based upon) the specific type of unsafe or unhealthy condition that is identified. For example, a lightning strike occurring at or near a particular home environment may affect other home environments within a particular radius, but may not affect other home environments that are further away.

In some examples, the home condition alert application 128 may transmit or otherwise display the alert by the various mobile computing devices 102 in real-time, upon identifying and/or detecting the unsafe or unhealthy condition that exists in the home environment 114.

Furthermore, in some examples, the home condition alert application 128 may only transmit the alert to (or display the alert by) mobile computing device 102 associated with the resident upon both (i) identifying the unsafe or unhealthy condition that exists in the home environment 114 or that may be developing in the home environment 114 over the period of time, and (ii) determining that the resident associated with the home environment 114 is not (or was not) physically present at the home environment 114 over the period of time.

Additionally, in some examples, the home condition alert application 128 may determine a distance (or attempt to determine the distance) between the resident of the home environment 114 and the home environment, and may only transmit the alert to (or display the alert by) mobile computing devices 102 associated with emergency contacts of the resident of the home environment 114 based upon determining that that the distance is greater than a threshold distance, or by failing to determine the distance.

Moreover, in some examples, the computer-readable instructions stored on the memory 126 may include instructions for carrying out any of the steps of the methods 200 via an algorithm executing on the processors 124, which are described in greater detail below with respect to FIG. 2.

In some embodiments the computing system 104 may comprise one or more servers, which may comprise multiple, redundant, or replicated servers as part of a server farm. In still further aspects, such server(s) may be implemented as cloud-based servers, such as a cloud-based computing platform. For example, such server(s) may be any one or more cloud-based platform(s) such as MICROSOFT AZURE, AMAZON AWS, or the like. Such server(s) may include one or more processor(s) 130 (e.g., CPUs) as well as one or more computer memories 132.

Memories 132 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others. Memorie(s) 132 may store an operating system (OS) (e.g., Microsoft Windows, Linux, UNIX, etc.) capable of facilitating the functionalities, apps, methods, or other software as discussed herein. Memorie(s) 132 may also store a home condition diagnostic application 134, a machine learning model training application 136, and/or a home condition diagnostic machine learning model 138.

Additionally, or alternatively, the memorie(s) 132 may store historical home condition diagnostic data. The historical home condition diagnostic data may include historical sensor data or operational data associated with historical home environments over historical periods of time, as well as identified unsafe or unhealthy conditions associated with historical home environments over the historical periods of time. The historical home condition diagnostic data may also be stored in a historical home condition diagnostic database 140, which may be accessible or otherwise communicatively coupled to the computing system 104. In some embodiments, the historical home condition diagnostic data, or other data from various sources may be stored on one or more blockchains or distributed ledgers.

Executing the home condition diagnostic application 134 may include receiving sensor data and/or operational data associated with the home environment over a period of time from the home condition alert application 128 of the mobile device 102, applying a trained home condition diagnostic machine learning model 138 to the sensor data and/or operational data from the period of time in order to identify unsafe or unhealthy conditions associated with the home environment over the period of time, and sending indications of the identified unsafe or unhealthy conditions associated with the home environment over the period of time to the home condition alert application 128 of the mobile device 102. In some embodiments, the sensor data, operational data, and/or mobile device data, and other data mentioned herein from various sources, may also be stored on one or more blockchains or distributed ledgers.

In some examples, the trained home condition diagnostic machine learning model 138 may be executed on the computing system 104, while in other examples the home condition diagnostic machine learning model 138 may be executed on another computing system, separate from the computing system 104. For instance, the computing system 104 may send the sensor data and/or operational data associated with the home environment over the period of time from the mobile device 102 to another computing system, where the trained home condition diagnostic machine learning model 138 is applied to the sensor data and/or operational data associated with the home environment over the period of time, and the other computing system may send a prediction or identification of unsafe or unhealthy conditions associated with the home environment over the period of time based upon applying the trained home condition diagnostic machine learning model 138 to the sensor data and/or the operational data associated with the home environment over the period of time, to the computing system 104. Moreover, in some examples, the home condition diagnostic machine learning model 138 may be trained by a machine learning model training application 136 executing on the computing system 104, while in other examples, the home condition diagnostic machine learning model 138 may be trained by a machine learning model training application executing on another computing system, separate from the computing system 104.

Whether the home condition diagnostic machine learning model 138 is trained on the computing system 104 or elsewhere, the home condition diagnostic machine learning model 138 may be trained by the machine learning model training application 136 using training data corresponding to historical sensor data and/or historical operational data associated with home environments over historical periods of time, and historical unsafe or unhealthy conditions associated with the home environment over the historical periods of time. The trained machine learning model may then be applied to new sensor data and/or new operational data over a new period of time in order to identify or predict, e.g., new unsafe or unhealthy conditions associated with the home environment over the new period of time.

In various aspects, the home condition diagnostic machine learning model 138 may comprise a machine learning program or algorithm that may be trained by and/or employ a neural network, which may be a deep learning neural network, or a combined learning module or program that learns in one or more features or feature datasets in particular area(s) of interest. The machine learning programs or algorithms may also include natural language processing, semantic analysis, automatic reasoning, regression analysis, support vector machine (SVM) analysis, decision tree analysis, random forest analysis, K-Nearest neighbor analysis, naïve Bayes analysis, clustering, reinforcement learning, and/or other machine learning algorithms and/or techniques.

In some embodiments, the artificial intelligence and/or machine learning based algorithms used to train the home condition diagnostic machine learning model 138 may comprise a library or package executed on the computing system 104 (or other computing devices not shown in FIG. 1). For example, such libraries may include the TENSORFLOW based library, the PYTORCH library, and/or the SCIKIT-LEARN Python library.

Machine learning may involve identifying and recognizing patterns in existing data (such as training a model based upon historical sensor data and/or operational data associated with a home environment over the period of time) in order to facilitate making predictions or identification for subsequent data (such as using the machine learning model on new sensor data and/or operational data in order to determine a prediction or identification of new unsafe or unhealthy conditions associated with the home environment over a new period of time).

Machine learning model(s) may be created and trained based upon example data (e.g., "training data") inputs or data (which may be termed "features" and "labels") in order to make valid and reliable predictions for new inputs, such as testing level or production level data or inputs. In supervised machine learning, a machine learning program operating on a server, computing device, or otherwise processor(s), may be provided with example inputs (e.g., "features") and their associated, or observed, outputs (e.g., "labels") in order for the machine learning program or algorithm to determine or discover rules, relationships, patterns, or otherwise machine learning "models" that map such inputs (e.g., "features") to the outputs (e.g., labels), for example, by determining and/or assigning weights or other metrics to the model across its various feature categories. Such rules, relationships, or otherwise models may then be provided subsequent inputs in order for the model, executing on the server, computing device, or otherwise processor(s), to predict, based upon the discovered rules, relationships, or model, an expected output.

In unsupervised machine learning, the server, computing device, or otherwise processor(s), may be required to find its own structure in unlabeled example inputs, where, for example multiple training iterations are executed by the server, computing device, or otherwise processor(s) to train multiple generations of models until a satisfactory model, e.g., a model that provides sufficient prediction accuracy when given test level or production level data or inputs, is generated. The disclosures herein may use one or both of such supervised or unsupervised machine learning techniques.

In addition, memories 132 may also store additional machine readable instructions, including any of one or more application(s), one or more software component(s), and/or one or more application programming interfaces (APIs), which may be implemented to facilitate or perform the features, functions, or other disclosure described herein, such as any methods, processes, elements or limitations, as illustrated, depicted, or described for the various flowcharts, illustrations, diagrams, figures, and/or other disclosure herein. For instance, in some examples, the computer-readable instructions stored on the memory 132 may include instructions for carrying out any of the steps of the method 200 via an algorithm executing on the processors 130, which are described in greater detail below with respect to FIG. 2. It should be appreciated that one or more other applications may be envisioned and that are executed by the processor(s) 130. It should be appreciated that given the state of advancements of mobile computing devices, all of the processes functions and steps described herein may be present together on a mobile computing device, such as the mobile computing device 102.

Figure 2:
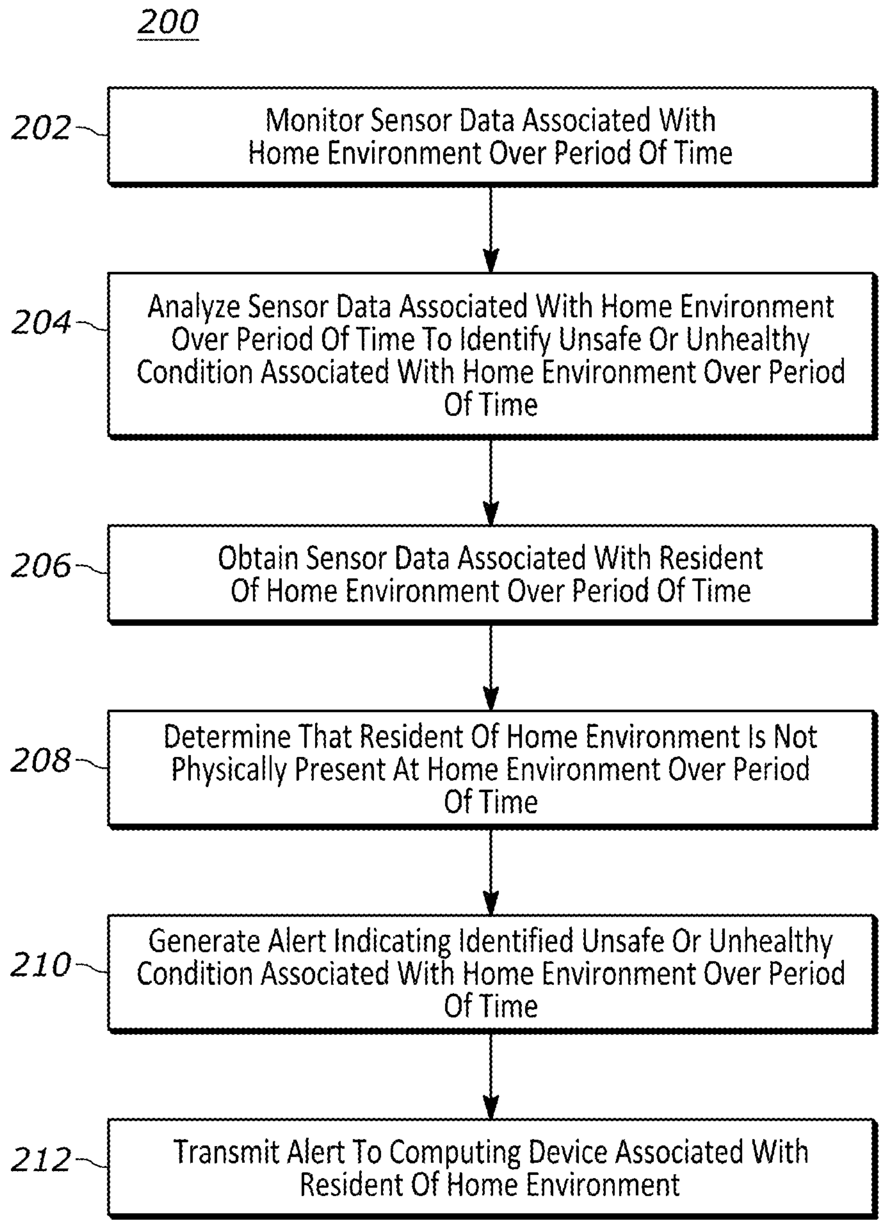
FIG. 2 depicts a flow diagram of an exemplary computer-implemented for generating alerts related to unsafe or unhealthy home conditions, according to one embodiment.

Exemplary Computer-Implemented Method for Generating Alerts Related to Unsafe or Unhealthy Home Conditions FIG. 2 depicts a flow diagram of an exemplary computer-implemented method 200 for generating alerts related to unsafe or unhealthy home conditions, according to one embodiment. One or more steps of the method 200 may be implemented as a set of instructions stored on a computer-readable memory (e.g., memory 126, memory 132, etc.) and executable on one or more processors (e.g., processor 124, processor 130, etc.).

The method may begin when sensor data associated with a home environment is monitored (block 202) over a period of time. In some examples, operational data associated with the home environment may also be monitored over the period of time.

The sensor data (and/or the operational data) associated with the home environment over the period of time may be analyzed (block 204) in order to identify an unsafe or unhealthy condition associated with the home environment over the period of time. In some examples, analyzing the sensor data (and/or the operational data) associated with the home environment over the period of time may include analyzing the sensor data (and/or the operational data) associated with the home environment over the period of time by applying a trained machine learning model to the sensor data (and/or operational data) associated with the home environment over the period of time.

For example, training the machine learning model may include obtaining historical sensor data (and/or historical operational data) associated with historical home environments over historical periods of time, and indications of historical unsafe or unhealthy conditions associated with the historical home environments over the historical periods of time, and training the machine learning model to identify new unsafe or unhealthy conditions in new home environments over new periods of time based upon new sensor data (and/or new operational data) associated with the new home environments, using the historical sensor data (and/or historical operational data) associated with historical home environments over historical periods of time, and the indications of historical unsafe or unhealthy conditions associated with the historical home environments over the historical periods of time, resulting in the trained machine learning model.

Sensor data associated with a resident of the home environment over the period of time may be obtained (block 206). In some examples, the sensor data associated with the resident of the home environment may include data captured by sensors of a mobile computing device associated with the resident of the home environment. Furthermore, in some examples, the sensor data associated with the resident of the home environment may include data captured by sensors associated with a vehicle owned or operated by the resident of the home environment. Additionally, in some examples, operational data associated with a vehicle owned or operated by the resident of the home environment may be obtained.

Based upon the sensor data associated with the resident of the home environment (and/or the operational data associated with the vehicle owned by or operated by the resident of the home environment) over the period of time, a determination (block 208) may be made that the resident of the home environment is not physically present at the home environment over the period of time. In some examples, this determination may be based upon applying a trained machine learning model (which may be the same machine learning model described with respect to block 204, or may be a different machine learning model) to the sensor data associated with the resident of the home environment (and/or the operational data associated with the vehicle owned by or operated by the resident of the home environment) over the period of time.

For example, training the machine learning model may include obtaining historical sensor data associated with residents of historical home environments (and/or historical operational data associated with historical vehicles owned by or operated by the residents of the historical home environments) over historical periods of time, and indications of whether the residents were physically present at the historical home environments over the historical periods of time, and training the machine learning model to determine whether residents of home environments are physically present at the home environments over new periods of time based upon new sensor data associated with the residents of the home environments (and/or new operational data associated with the vehicle owned by or operated by the resident of the home environment) over new periods of time, using the historical sensor data associated with residents of historical home environments (and/or the historical operational data associated with the vehicles owned by or operated by the residents of the historical home environments) over historical periods of time, and indications of whether the residents were physically present at the historical home environments over the historical periods of time, resulting in the trained machine learning model.

Upon identifying an unsafe or unhealthy condition associated with the home environment over the period of time and determining that the resident of the home environment is not physically present at the home environment over the period of time, an alert may be generated (block 210), indicating the identified unsafe or unhealthy condition associated with the home environment over the period of time.

The generated alert may be transmitted (block 212) to a computing device associated with the resident of the home environment. In some examples, a distance between a first location associated with the home environment and a second location associated with the resident of the home environment over the period of time may be determined, or may be attempted to be determined. If the distance between the first location associated with the home environment and the second location associated with the resident of the home environment over the period of time is greater than a threshold distance, or if the location associated with the resident of the home environment over the period of time cannot be determined, the alert may additionally (or alternatively) be transmitted to a computing device associated with a neighbor or other emergency contact.

In some examples, the method 200 may further include determining a likelihood that the unsafe or unhealthy condition associated with the home environment over the period of time will result in unsafe or unhealthy conditions for one or more other home environments, e.g., other home environments within a given geographic radius of the home environment for which the unsafe or unhealthy condition was identified. In some examples, the relevant geographic radius may be based upon the particular unsafe or unhealthy condition that is identified (e.g., certain unsafe or unhealthy conditions may be more likely to affect only homes next door to the original home, while other unsafe or unhealthy conditions may affect an entire apartment complex, neighborhood, or subdivision). If the likelihood is greater than a threshold likelihood (e.g., greater than 50%, greater than 75%, etc.) the alert may be transmitted to computing devices associated with the respective one or more other home environments. In some examples, the originally generated alert may be modified, customized, or otherwise tailored to the one or more other home environments. In some examples, the residents of the other home environments may be prompted to confirm whether the identified unsafe or unhealthy condition exists at their respective home environments after receiving the alert.

Figure 3:
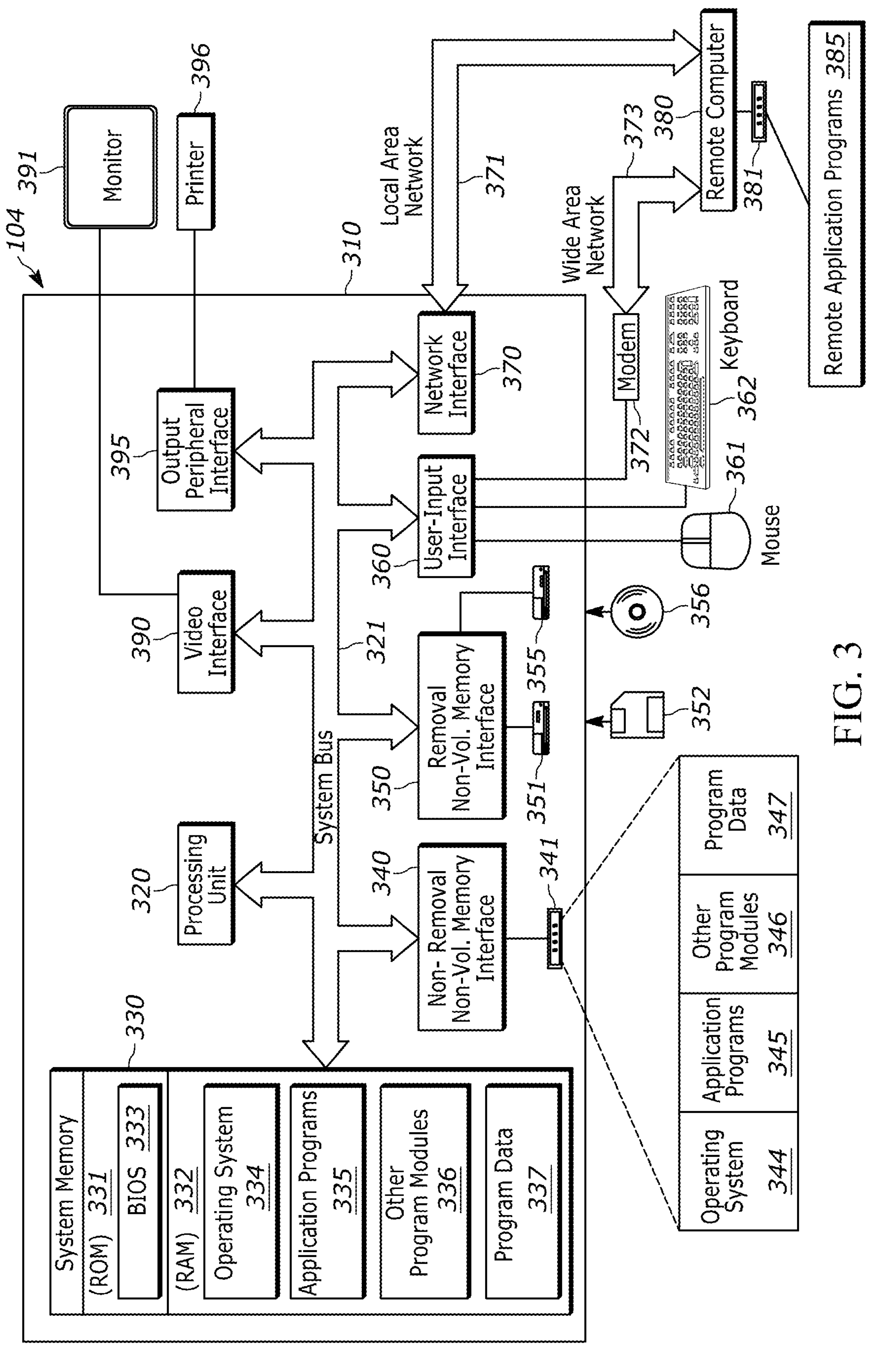
FIG. 3 depicts an exemplary computing system in which the techniques described herein may be implemented, according to one embodiment.

Exemplary Computing System for Generating Alerts Related to Unsafe or Unhealthy Home Conditions FIG. 3 depicts an exemplary computing system 104 in which the techniques described herein may be implemented, according to one embodiment. The computing system 104 of FIG. 3 may include a computing device in the form of a computer 310. Components of the computer 310 may include, but are not limited to, a processing unit 320 (e.g., corresponding to the processor 120 of FIG. 1), a system memory 330 (e.g., corresponding to the memory 122 of FIG. 1), and a system bus 321 that couples various system components including the system memory 330 to the processing unit 320. The system bus 321 may be any of several types of bus structures including a memory bus or memory controller, a peripheral bus, or a local bus, and may use any suitable bus architecture. By way of example, and not limitation, such architectures include the Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus (also known as Mezzanine bus).

Computer 310 may include a variety of computer-readable media. Computer-readable media may be any available media that can be accessed by computer 310 and may include both volatile and nonvolatile media, and both removable and non-removable media. By way of example, and not limitation, computer-readable media may comprise computer storage media and communication media.

Computer storage media may include volatile and nonvolatile, removable and non-removable media implemented in any method or technology for storage of information such as computer-readable instructions, data structures, program modules or other data. Computer storage media may include, but is not limited to, RAM, ROM, EEPROM, FLASH memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 310.

Communication media typically embodies computer-readable instructions, data structures, program modules or other data in a modulated data signal such as a carrier wave or other transport mechanism, and may include any information delivery media. The term "modulated data signal" means a signal that has one or more of its characteristics set or changed in such a manner as to encode information in the signal. By way of example, and not limitation, communication media may include wired media such as a wired network or direct-wired connection, and wireless media such as acoustic, radio frequency (RF), infrared and other wireless media. Combinations of any of the above are also included within the scope of computer-readable media.

The system memory 330 may include computer storage media in the form of volatile and/or nonvolatile memory such as read only memory (ROM) 331 and random access memory (RAM) 332. A basic input/output system 333 (BIOS), containing the basic routines that help to transfer information between elements within computer 310, such as during start-up, is typically stored in ROM 331. RAM 332 typically contains data and/or program modules that are immediately accessible to, and/or presently being operated on, by processing unit 320. By way of example, and not limitation, FIG. 3 illustrates operating system 334, application programs 335 (e.g., corresponding to the home condition diagnostic application 134, machine learning model training application 136, home condition diagnostic machine learning model 138, etc.), other program modules 336, and program data 337.

The computer 310 may also include other removable/non-removable, volatile/nonvolatile computer storage media. By way of example only, FIG. 3 illustrates a hard disk drive 341 that reads from or writes to non-removable, nonvolatile magnetic media, a magnetic disk drive 351 that reads from or writes to a removable, nonvolatile magnetic disk 352, and an optical disk drive 355 that reads from or writes to a removable, nonvolatile optical disk 356 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 341 may be connected to the system bus 321 through a non-removable memory interface such as interface 340, and magnetic disk drive 351 and optical disk drive 355 may be connected to the system bus 321 by a removable memory interface, such as interface 350.

The drives and their associated computer storage media discussed above and illustrated in FIG. 3 provide storage of computer-readable instructions, data structures, program modules and other data for the computer 310. In FIG. 3, for example, hard disk drive 341 is illustrated as storing operating system 344, application programs 345, other program modules 346, and program data 347. Note that these components may either be the same as or different from operating system 334, application programs 335, other program modules 336, and program data 337. Operating system 344, application programs 345, other program modules 346, and program data 347 are given different numbers here to illustrate that, at a minimum, they are different copies. A user may enter commands and information into the computer 310 through input devices such as cursor control device 361 (e.g., a mouse, trackball, touch pad, etc.) and keyboard 362. A monitor 391 or other type of display device is also connected to the system bus 321 via an interface, such as a video interface 390. In addition to the monitor, computers may also include other peripheral output devices such as printer 396, which may be connected through an output peripheral interface 395.

The computer 310 may operate in a networked environment using logical connections to one or more remote computers, such as a remote computer 380. The remote computer 380 may be a mobile computing device, personal computer, a server, a router, a network PC, a peer device or other common network node, and may include many or all of the elements described above relative to the computer 310, although only a memory storage device 381 has been illustrated in FIG. 3. The logical connections depicted in FIG. 3 include a local area network (LAN) 371 and a wide area network (WAN) 373 (e.g., either or both of which may correspond to the network 108 of FIG. 1), but may also include other networks. Such networking environments are commonplace in hospitals, offices, enterprise-wide computer networks, intranets and the Internet.

When used in a LAN networking environment, the computer 310 is connected to the LAN 371 through a network interface or adapter 370. When used in a WAN networking environment, the computer 310 may include a modem 372 or other means for establishing communications over the WAN 373, such as the Internet. The modem 372, which may be internal or external, may be connected to the system bus 321 via the input interface 360, or other appropriate mechanism. The communications connections 370, 372, which allow the device to communicate with other devices, are an example of communication media, as discussed above. In a networked environment, program modules depicted relative to the computer 310, or portions thereof, may be stored in the remote memory storage device 381. By way of example, and not limitation, FIG. 3 illustrates remote application programs 385 as residing on memory device 381.

The techniques for generating alerts related to unsafe or unhealthy home conditions described above may be implemented in part or in their entirety within a computing system such as the computing system 104 illustrated in FIG. 3. In some such embodiments, the LAN 371 or the WAN 373 may be omitted. Application programs 335 and 345 may include a software application (e.g., a web-browser application) that is included in a user interface, for example.

ADDITIONAL CONSIDERATIONS

The following additional considerations apply to the foregoing discussion. Throughout this specification, plural instances may implement operations or structures described as a single instance. Although individual operations of one or more methods are illustrated and described as separate operations, one or more of the individual operations may be performed concurrently, and nothing requires that the operations be performed in the order illustrated. These and other variations, modifications, additions, and improvements fall within the scope of the subject matter herein.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" or "some embodiments" means that a particular element, feature, structure, or characteristic described in connection with the embodiment is included in at least one embodiment. The appearances of the phrase "in one embodiment" or "in some embodiments" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of "a" or "an" is employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for generating alerts related to unsafe or unhealthy home conditions. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A computer-implemented method for generating an alert related to an unsafe or unhealthy condition associated with a home environment, comprising:

monitoring, by one or more processors, sensor data associated with the home environment over a period of time;

analyzing, by the one or more processors, the sensor data associated with the home environment over the period of time in order to identify the unsafe or unhealthy condition associated with the home environment over the period of time;

obtaining, by the one or more processors, data associated with a resident of the home environment over the period of time, wherein the data associated with the resident of the home environment includes one or more of:

wireless connectivity data associated with one or more of: (i) a mobile device associated with the resident or (ii) a vehicle associated with the resident, or sensor data from one or more of: (i) the mobile device associated with the resident or (ii) the vehicle associated with the resident;

determining, by the one or more processors, based upon the data associated with the resident of the home environment over the period of time, that the resident of the home environment is not physically present at the home environment over the period of time; and upon identifying the unsafe or unhealthy condition associated with the home environment over the period of time and determining that the resident of the home environment is not physically present at the home environment over the period of time, generating the alert, by the one or more processors, the alert indicating the identified unsafe or unhealthy condition associated with the home environment over the period of time.

2. The computer-implemented method of claim 1, further comprising:

determining, by the one or more processors, a likelihood that the unsafe or unhealthy condition associated with the home environment over the period of time will result in unsafe or unhealthy conditions for one or more other home environments; and based upon the likelihood being greater than a threshold likelihood, transmitting the alert to computing devices associated with the respective one or more other home environments.

3. The computer-implemented method of claim 2, wherein transmitting the alert to the computing devices associated with the respective one or more other home environments includes:

prompting, by the one or more processors, residents of the respective one or more other home environments to confirm whether an unsafe or unhealthy condition exists at the respective one or more other home environments.

4. The computer-implemented method of claim 1, further comprising:

determining, by the one or more processors, a distance between a first location associated with the home environment and a second location associated with the resident of the home environment over the period of time; and based upon the distance between the first location and the second location being greater than a threshold distance, transmitting the alert to a computing device associated with an emergency contact of the resident of the home environment.

5. The computer-implemented method of claim 1, further comprising:

attempting to determine, by the one or more processors, a location associated with the resident of the home environment over the period of time; and based upon a failure to determine the location associated with the resident of the home environment over the period of time, transmitting the alert to a computing device associated with an emergency contact of the resident of the home environment.

6. The computer-implemented method of claim 1, wherein analyzing the sensor data associated with the home environment over the period of time in order to identify the unsafe or unhealthy condition associated with the home environment over the period of time includes applying a trained machine learning model to the sensor data associated with the home environment over the period of time in order to identify the unsafe or unhealthy condition associated with the home environment over the period of time.

7. The computer-implemented method of claim 6, further comprising:

obtaining, by the one or more processors, historical sensor data associated with historical home environments over historical periods of time, and indications of historical unsafe or unhealthy conditions associated with the historical home environments over the historical periods of time; and training, by the one or more processors, a machine learning model to identify new unsafe or unhealthy conditions in new home environments over new periods of time based upon new sensor data associated with the new home environments, using the historical sensor data associated with historical home environments over historical periods of time, and the indications of historical unsafe or unhealthy conditions associated with the historical home environments over the historical periods of time, resulting in the trained machine learning model.

8. The computer-implemented method of claim 1, wherein determining that the resident of the home environment is not physically present at the home environment over the period of time, based upon the data associated with the resident of the home environment over the period of time, includes applying a trained machine learning model to the data associated with the resident of the home environment over the period of time in order to determine that the resident of the home environment is not physically present at the home environment over the period of time.

9. The computer-implemented method of claim 8, further comprising:

obtaining, by the one or more processors, historical data associated with residents of historical home environments over historical periods of time, and indications of whether the residents were physically present at the historical home environments over the historical periods of time; and training, by the one or more processors, a machine learning model to determine whether residents of home environments are physically present at the home environments over new periods of time based upon new data associated with the residents of the home environments, using the historical data associated with residents of historical home environments over historical periods of time, and indications of whether the residents were physically present at the historical home environments over the historical periods of time, resulting in the trained machine learning model.

10. A system for generating an alert related to an unsafe or unhealthy condition associated with a home environment, comprising one or more processors, and a non-transitory memory storing computer-readable instructions that when executed by the one or more processors, causes the one or more processors to:

monitor sensor data associated with the home environment over a period of time;

analyze the sensor data associated with the home environment over the period of time in order to identify the unsafe or unhealthy condition associated with the home environment over the period of time;

obtain data associated with a resident of the home environment over the period of time, wherein the data associated with the resident of the home environment includes one or more of:

wireless connectivity data associated with one or more of: (i) a mobile device associated with the resident or (ii) a vehicle associated with the resident, or sensor data from one or more of: (i) the mobile device associated with the resident or (ii) the vehicle associated with the resident;

determine, based upon the data associated with the resident of the home environment over the period of time, that the resident of the home environment is not physically present at the home environment over the period of time; and upon identifying the unsafe or unhealthy condition associated with the home environment over the period of time and determining that the resident of the home environment is not physically present at the home environment over the period of time, generate the alert indicating the identified unsafe or unhealthy condition associated with the home environment over the period of time.

11. A non-transitory computer-readable medium for generating an alert related to an unsafe or unhealthy condition associated with a home environment storing computer-readable instructions that, when executed by one or more processors, causes the one or more processors to:

monitor sensor data associated with the home environment over a period of time;

analyze the sensor data associated with the home environment over the period of time in order to identify the unsafe or unhealthy condition associated with the home environment over the period of time;

obtain data associated with a resident of the home environment over the period of time, wherein the data associated with the resident of the home environment includes one or more of:

wireless connectivity data associated with one or more of: (i) a mobile device associated with the resident or (ii) a vehicle associated with the resident, or sensor data from one or more of: (i) the mobile device associated with the resident or (ii) the vehicle associated with the resident;

determine, based upon the data associated with the resident of the home environment over the period of time, that the resident of the home environment is not physically present at the home environment over the period of time; and upon identifying the unsafe or unhealthy condition associated with the home environment over the period of time and determining that the resident of the home environment is not physically present at the home environment over the period of time, generate the alert indicating the identified unsafe or unhealthy condition associated with the home environment over the period of time.

* * * * *